(12) United States Patent
Villard et al.

(10) Patent No.: US 9,638,618 B2
(45) Date of Patent: May 2, 2017

(54) ONLINE MEASURING ASSEMBLY OF THE RHEOLOGICAL PROPERTIES OF A DRILLING FLUID AND ASSOCIATED MEASURING METHOD

(75) Inventors: Eric Villard, Ver-sur-Launette (FR); Namic Klioua, Paris (FR)

(73) Assignee: GEOSERVICES EQUIPMENTS, Roissy en France (FR)

( * ) Notice: Subject to any disclaimer, the term of this patent is extended or adjusted under 35 U.S.C. 154(b) by 1025 days.

(21) Appl. No.: 13/575,611

(22) PCT Filed: Jan. 26, 2011

(86) PCT No.: PCT/EP2011/051082
§ 371 (c)(1),
(2), (4) Date: Sep. 20, 2012

(87) PCT Pub. No.: WO2011/092213
PCT Pub. Date: Aug. 4, 2011

(65) Prior Publication Data
US 2013/0009784 A1   Jan. 10, 2013

(30) Foreign Application Priority Data
Jan. 27, 2010 (FR) .................................. 10 50538

(51) Int. Cl.
  *G01V 3/00*  (2006.01)
  *G01N 11/14*  (2006.01)
  *G01N 1/14*  (2006.01)

(52) U.S. Cl.
  CPC ............... *G01N 11/14* (2013.01); *G01N 1/14* (2013.01)

(58) Field of Classification Search
  None
  See application file for complete search history.

(56) References Cited

U.S. PATENT DOCUMENTS 3,777,551 A * 12/1973 Weiss ................. G01N 11/14
                                                             73/54.28
4,484,468 A * 11/1984 Gau .................... G01N 11/14
                                                             702/50

(Continued)

FOREIGN PATENT DOCUMENTS

| EP | 0211112 | 2/1987 |
|---|---|---|
| WO | 2009055672 A1 | 4/2009 |
| WO | 2009/153603 | 12/2009 |

OTHER PUBLICATIONS

Communication pursuant to Article 94(3) EPC in the related EP Application, 11700952.2, dated Dec. 7, 2016 (6 pages).

*Primary Examiner* — Amine Benlagsir
(74) *Attorney, Agent, or Firm* — Michael Dae (57) ABSTRACT

This assembly includes a measuring device (50) including a container (60) and an insert (62) arranged in the container (60). The measuring device (50) includes a means (68) for driving the container (60) in rotation around a central axis, the container (60) and the insert (62) defining an intermediate space (64) between them for measuring the drilling fluid. The assembly includes a control and measurement unit (58), capable of recording information representative of the force applied by the drilling fluid on the insert (62) during the rotation of the container (60). The assembly includes an intake pipe (84) for bringing drilling fluid to be measured into the intermediate space (94) and a pump (82), comprising an inlet connected to a sampling head (80) and an outlet connected to the intake pipe (84) to pump the drilling fluid towards the intermediate space (64).

14 Claims, 6 Drawing Sheets

(56) References Cited

U.S. PATENT DOCUMENTS

| | | | |
|---|---|---|---|
| 4,614,236 A * | 9/1986 | Watkins | C09K 8/26 |
| | | | 134/36 |
| 4,703,664 A | 11/1987 | Kirkpatrick et al. | |
| 5,269,632 A * | 12/1993 | Pelletier | C09K 17/02 |
| | | | 106/607 |
| 5,964,295 A * | 10/1999 | Brown | C09K 8/68 |
| | | | 166/308.2 |
| 6,443,001 B1 | 9/2002 | Duriez et al. | |
| 6,763,888 B1 * | 7/2004 | Harris | C09K 8/52 |
| | | | 166/300 |
| 7,531,483 B2 * | 5/2009 | Pena | C09K 8/52 |
| | | | 166/278 |
| 7,669,653 B2 * | 3/2010 | Craster | E21B 23/06 |
| | | | 166/101 |
| 2002/0023752 A1 * | 2/2002 | Qu | C09K 8/68 |
| | | | 166/308.1 |
| 2002/0169085 A1 * | 11/2002 | Miller | C09K 8/685 |
| | | | 507/200 |
| 2006/0075801 A1 * | 4/2006 | Evrard | E21B 21/067 |
| | | | 73/19.09 |
| 2007/0215346 A1 | 9/2007 | Sloan et al. | |
| 2008/0020948 A1 * | 1/2008 | Rodrigues | C02F 5/10 |
| | | | 507/112 |
| 2010/0250142 A1 * | 9/2010 | Zamora | E21B 49/08 |
| | | | 702/12 |

\* cited by examiner

ONLINE MEASURING ASSEMBLY OF THE RHEOLOGICAL PROPERTIES OF A DRILLING FLUID AND ASSOCIATED MEASURING METHOD

FIELD

The present disclosure relates to an online measuring assembly of the rheological properties of a drilling fluid and, more particularly, relates to the system and associated method for obtaining continuous high quality samples.

BACKGROUND

During drilling of an oil well or another effluent (in particular gas, vapor, water), it is known to analyze the drilling fluid emerging from the well in order to obtain useful information on the well being drilled.

To that end, by analyzing, for example, the gaseous compounds and the drilling debris contained in the drilling mud emerging from the well, it is possible to reconstitute the geological succession of the formations passed through during the drilling, which plays a role in determining exploitation possibilities of the fluid deposits encountered.

Moreover, a certain number of other analyses are done on the drilling fluid emerging from the well or possibly injected into the well. To that end, it is known to recover, at regular intervals, samples of drilling fluid and to analyze those samples in a laboratory present on the drilling site. These analyses comprise in particular the determination of the rheological properties of the drilling fluid to determine its viscosity. The drilling fluid is in fact generally a non-newtonian fluid, or even a thixotropic fluid.

This analysis is intended in particular to assess the behavior of the fluid during different drilling phases.

In particular, when the drilling is stopped for a fairly long period of time, the drilling fluid present in the well can have a notable increase in viscosity, which must be taken into account when the pumps ensuring circulation of the drilling fluid in the well are restarted.

The measurement of the rheological properties of a fluid is generally done according to the standards recommended by the American Petroleum Institute (API). To that end, a drilling fluid sample is taken at regular intervals by the operator, for example at a mud pit. The recovered sample is then conveyed by the operator to the measuring booth where it is placed in a measuring assembly of the aforementioned type, as described in U.S. Pat. No. 4,484,468, for example.

Such a measuring assembly generally includes a rotary hollow container, able to be driven in rotation at chosen speeds of rotation. It also includes a pin arranged in the hollow container and delimiting, with the container, an intermediate space receiving the fluid to be measured.

The pin is mounted partially free in rotation around its axis. During the measurement, the container is driven in rotation around its axis at a given speed of rotation, which partially drives the drilling fluid in rotation under the effect of the shearing. Information representative of the force applied by the drilling fluid on the pin during the rotation of the container is collected by a sensor. The sensor for example measures the degree of rotation of the insert around its axis for different speeds of rotation of the container.

Such a device is not completely satisfactory. It in fact requires significant labor and continuous interventions on the well, in particular in the secured zone around the well.

In fact, this measurement is typically only done 4 to 6 times per day, which does not make it possible to identify all of the rheological changes.

Moreover, the precision of the measurement depends on the quality of the sample taken by the operator, and also the quality of the measurement done by the operator.

One aim of the disclosure is therefore to obtain an assembly for measuring the rheological properties of a drilling fluid, that is simple and reliable to use, in particular on a drilling site, and that nevertheless makes it possible to obtain precise and reproducible measurements, in particular according to the existing standards.

SUMMARY

The present disclosure relates to an online measuring assembly of the rheological properties of a drilling fluid. The assembly includes a measuring device including a hollow container with a central axis and an insert arranged in the container, at least one of the container and the insert being rotatably mounted around the central axis, the measuring device including a means for driving the rotation of one of the container and the insert around the central axis; the container and the insert defining an intermediate space between them for measuring the drilling fluid;

a control and measurement unit, capable of activating the means for driving in rotation to drive one of the container and the insert in rotation at a chosen speed and capable of recording information representative of the force applied by the drilling fluid on the other of the container and the insert during the rotation of one of the container and the insert.

an intake pipe for the drilling fluid to be measured in the intermediate measuring space and a discharge pipe for the drilling fluid outside the intermediate measuring space;

a pump having an inlet connected to a drilling fluid sampling head in a drilling fluid volume and an outlet connected to the intake pipe to pump the drilling fluid outside the sampling head towards the intermediate measuring space.

The assembly according to the disclosure can include one or several of the following features, considered alone or according to all technically possible combinations:

the assembly includes an injection pipe for injecting a cleaning fluid, separate from the intake pipe and the discharge pipe, the injection pipe emerging in the intermediate measuring space, the assembly advantageously having an auxiliary pump for injecting cleaning fluid having an outlet connected to the injection pipe;

the assembly includes a means for injecting a pressurized purge gas into the intermediate measuring space, capable of ejecting the drilling fluid present in the intermediate measuring space before injecting cleaning fluid through the injection pipe;

the assembly includes a module for regulating the temperature of the drilling fluid brought into the intermediate measuring space, the temperature regulating module advantageously being inserted between the sampling head and the container;

the assembly includes a degassing module, capable of extracting the gas present in the drilling fluid to evacuate it outside the drilling fluid, the degassing module being inserted between the sampling head and the container;

the control and measuring unit includes a means for steering the pump capable of activating the pump in a first measuring phase to continuously inject drilling fluid at a given flow rate into the intermediate measuring space, the steering means being capable of stopping the pump during a predetermined time in a second phase for immobilizing the fluid in the intermediate measuring space, then being capable of reactivating the pump in a second measuring phase similar to the first measuring phase; and the control and measuring unit includes means for recording the temporal variation of the information representative of the force applied by the drilling fluid on the other of the insert and the container, capable of continuously recording the temporal variation of the representative information during the second stopped phase of the pump.

The disclosure also relates to a method for online measurement of the rheological properties of a drilling fluid, of the type comprising the following steps:

provision of an assembly as defined above;

activation of the pump to continuously pump the drilling fluid from the sampling head, through the fluid intake pipe in the intermediate measuring space, the drilling fluid being evacuated outside the intermediate measuring space through the discharge pipe, driving in rotation around the central axis, at at least one given speed, one of the container and the insert using the means for driving in rotation;

measuring information representative of the force applied by the drilling fluid on the other of the container and the insert when one of the container and the insert is driven in rotation around the central axis.

The method according to the disclosure can comprise one or several of the following features, considered alone or according to all technically possible combinations:

the method includes, after a measuring step, the injection of a cleaning fluid in the intermediate measuring space through an injection pipe separate from the intake pipe and the discharge pipe, the injection pipe emerging in the intermediate measuring space;

the method includes, before the step for injecting cleaning fluid, a step for purging the intermediate measuring space using a pressurized gas to empty the fluid present in the intermediate measuring space before injecting cleaning fluid;

the method includes a step for regulating the temperature of the drilling fluid at a temperature chosen in a module for regulating the temperature arranged between the sampling head and the container;

the method includes a degassing step of the gas present in the drilling fluid to evacuate said gas outside the drilling fluid, the degassing step being performed in a degassing module positioned between the sampling head and the container;

the method includes a phase for calibrating the measurement depending on the temperature at a given speed of rotation of one of the container and the insert, the calibration phase including:

the successive provision in the intermediate measuring space of drilling fluid at at least two distinct calibration temperatures, and for each calibration temperature, the measurement of the representative information at the given speed, the determination of at least one calibration parameter of an equation connecting the representative information determined at one measurement temperature to the representative information calculated at a reference temperature different from the measurement temperature, the or each calibration parameter being obtained based on representative information measured at each calibration temperature, the measurement step comprising measuring the representative information of the drilling fluid brought into the intermediate measuring space, and measuring the measurement temperature of the drilling fluid, the method comprising a phase for calculating the representative information at the reference temperature, based on the representative information measured at the measurement temperature and the equation determined in the calibration step;

the calibration phase includes the following steps:

stopping the pump, measuring information representative of the force applied by the drilling fluid present at a first calibration temperature on the other of the container and the insert when one of the container and the insert is driven in rotation around the central axis;

cooling the drilling fluid present in the intermediate measuring space, then measuring information representative of the force applied by the drilling fluid present in the intermediate measuring space at at least one second calibration temperature lower than the first temperature on the other of the container and the insert when one of the container and the insert is driven in rotation around the central axis; and the method includes at least one phase for measuring the gel, including the following steps:

stopping the pump;

driving the drilling fluid present in the intermediate measuring space in rotation at a first speed for a given homogenization time;

immobilizing one of the container and the insert for a given idle time;

driving one of the container and the insert in rotation at a second speed lower than the first speed for a given measurement time;

measuring the information representative of the force applied by the drilling fluid on the other of the container and the insert for the given measuring time to determine the maximum value of the representative information as a function of the time during the given measuring time;

recording, at a given frequency, representative information measured during the entire given measuring time to obtain the temporal variation of the representative information before and after the maximum value.

In another exemplary embodiment, a method of measuring the rheological properties of a drilling fluid is disclosed. The method includes activating a pump to continuously pump a drilling fluid to the surface;

channeling the drilling fluid into a measuring assembly;

driving in rotation around the central axis, at at least one given speed, one of a container and an insert using means for driving in rotation;

measuring information representative of the force applied by the drilling fluid on the other of the container and the insert when one of the container and the insert is driven in rotation around the central axis, characterized in that the method includes compensating or calibrating the measurement depending on the temperature at a given speed of rotation of one of the container and the insert.

In another exemplary embodiment, a method of measuring the rheological properties of a drilling fluid is disclosed. The method includes
- activating a pump to continuously pump a drilling fluid to the surface;
- channeling the drilling fluid into a measuring assembly;
- measuring a maximum force related to at least one rheological property of the drilling fluid;
- characterized in that the post maximum force information is provided and utilized to obtain additional properties or parameters related to the fluid.

In another exemplary embodiment, a method of measuring the rheological properties of a drilling fluid is disclosed. The method includes
- activating a pump to continuously pump a drilling fluid to the surface;
- channeling the drilling fluid into a measuring assembly;
- measuring rheological properties of the drilling fluid;
- characterized in that the method further includes
- cleaning the measuring assembly with a cleaning fluid having known rheological properties;
- measuring the rheological properties of the cleaning fluid; and
- calibrating the measuring assembly based on the measured rheological properties of the cleaning fluid.

BRIEF DESCRIPTION OF THE DRAWINGS

The disclosure will be better understood upon reading the following description, provided solely as an example, and done in reference to the appended drawing, in which.

DETAILED DESCRIPTION

In all of the following, the terms "upstream" and "downstream" are used in reference to the normal direction of circulation of a fluid in a pipe.

A measuring assembly 10 according to the disclosure is for example used in a drilling installation 11 for oil production. This assembly 10 is intended to measure the rheological properties of the drilling fluid emerging from the well or injected into the well, online and substantially continuously.

"Substantially continuously" means in particular that a measurement done on the fluid can be done for a given time, and that another measurement can be done immediately at the end of the first measurement.

The measured rheological properties are in particular the shearing stress for different shearing rates applied on the drilling fluid. This makes it possible to evaluate the viscoelastic behavior of the drilling fluid.

Figure 1:
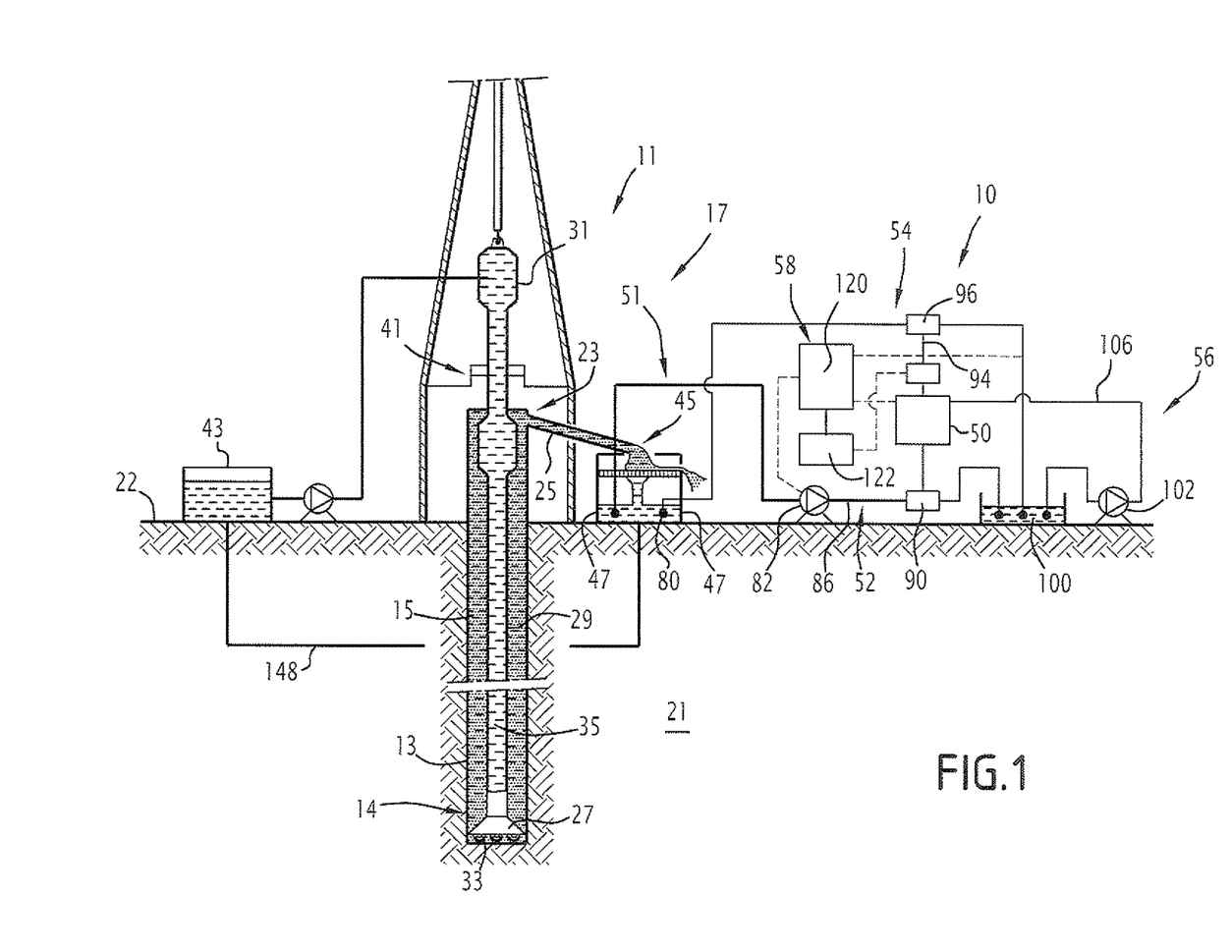
FIG. 1 is a diagrammatic vertical cross-sectional view of a drilling installation provided with a first measuring assembly according to the disclosure.

As illustrated in FIG. 1, the installation 11 comprises a drilling pipe 13 arranged in a cavity 14 pierced by a rotary drill tool 15, a surface installation 17, and the first measuring assembly 10 according to the disclosure.

The drilling pipe 13 is arranged in the cavity 14 formed in the subsoil 21 by the rotary drill tool 15. This pipe 13 includes, at the surface 22, a wellhead 23 provided with an emptying pipe 25.

The drill tool 15 comprises a drill head 27, a drill string 29, and an injection head 31 for injecting drilling fluid.

The drill head 27 comprises a means 33 for piercing rocks in the subsoil 21. It is mounted on the lower portion of the drill string 29 and is positioned in the bottom of the drill pipe 13.

The string 29 comprises a set of hollow drill tubes. These tubes delimit an internal space 35 that makes it possible to bring a liquid from the surface 22 to the drill head 27. To that end, the injection head 31 for injecting liquid is screwed on the upper portion of the string 29.

The surface installation 17 comprises a means 41 for support and driving in rotation of the drill tool 15, an injection means 43 for injecting drill fluid and a vibrating screen 45.

The injection means 43 is hydraulically connected to the injection head 31 to introduce and circulate the drilling fluid in the inner space 35 of the drill string 29.

The vibrating screen 45 collects the fluid charged with drilling residue that comes out of the emptying pipe 25 and separates the liquid from the solid drilling residue.

The surface installation 17 also includes a mud pit 47 capable of collecting the liquid received from the vibrating screen 45.

The drilling fluid is generally designated by the term "drill mud." The drill mud is for example a water drill mud, an oil drill mud, or a synthetic drill mud.

Figure 2:
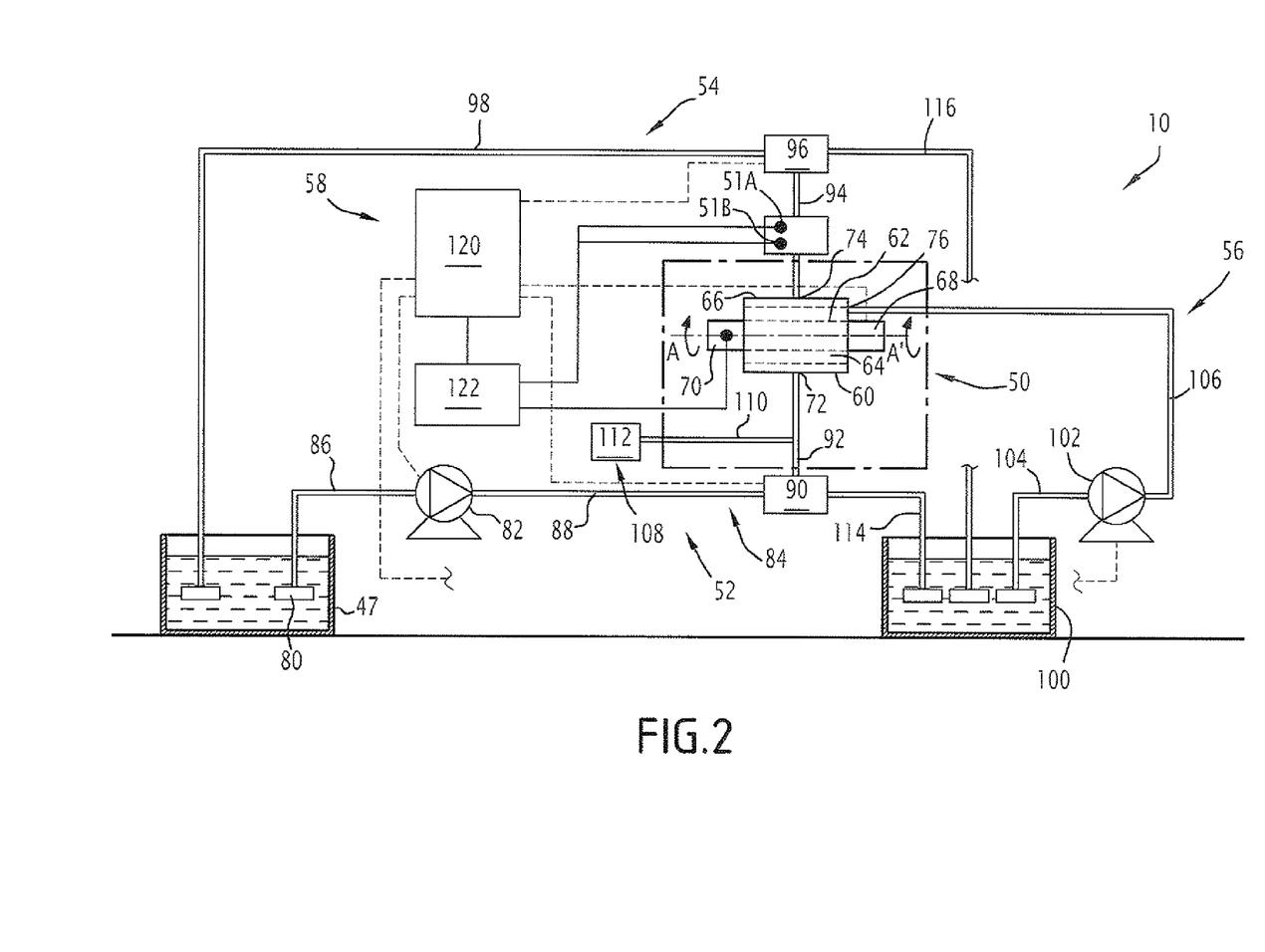
FIG. 2 is a diagrammatic view of the main elements of the measuring assembly shown in FIG. 1.

As illustrated by FIGS. 1 and 2, the measuring assembly 10 includes a device 50 for measuring rheological properties, measurement sensors 51A, 51B measuring the temperature and level, respectively, a transport means 52 for transporting the drilling fluid towards the measuring device 50, and a discharge means 54 for discharging the drilling fluid outside the measuring device 50.

The measuring assembly 10 also includes a means 56 for cleaning the measuring device 50 and a control and measurement unit 58.

The measuring device 50 includes a hollow container 60 with a central axis A-A', rotatably mounted around its axis, a pin 62 inserted in the hollow container 60, the hollow container 60 and the pin 62 defining an intermediate space 64 between them for receiving the measured drilling fluid.

The device 50 also comprises an outer jacket 66 intended to sealably contain the hollow container 60 and the pin 62, a mechanism 68 for driving the hollow container 60 in rotation around its axis A-A' and a sensor 70 for measuring the force applied on the pin 62 by the drilling fluid present in the intermediate space 64 during the rotation of the hollow container 60 around its axis A-A'.

In the example shown in FIG. 2, the measuring device 50 is a Couette viscosimeter. The hollow container 60 is then formed by a cylindrical sleeve. The axis A-A' of the container 60 is arranged horizontally, for example. The pin 62 is rotatably received around the axis A-A' in the hollow container 60. It is also cylindrical.

The intermediate space 64 is an annular space delimited between the pin 62 and the hollow container 60.

The jacket 66 defines an intake opening 72 for drilling fluid in the intermediate space 64, a discharge opening 74 for drilling fluid outside the intermediate space 64. The openings 72, 74 emerge opposite each other transversely relative to axis A-A'.

The jacket 66 also defines a plurality of cleaning fluid injection openings 76 that emerge directly in the intermediate space 64 at an axial end of said space 64. The injection openings 76 are for example formed in an annular crown axially covering the intermediate space 64.

The driving mechanism 68 can be controlled by the control unit 58 to drive the hollow container 60 in rotation around the axis A-A' at a plurality of adjustable constant speeds. The constant speed is for example between one revolution per minute and one thousand revolutions per minute, advantageously between 2 revolutions per minute and 450 revolutions per minute to apply a shearing rate from $5\ s^{-1}$ to $1050\ s^{-1}$.

The mechanism 68 is capable of maintaining the chosen constant speed for a determined period of time, steered by the control unit 58.

The pin 62 is mounted freely rotating around the axis A-A', while being subjugated towards a reference angular position around the axis A-A' by an elastic stressing means (not shown).

The sensor 70 is capable of measuring the angular deviation of the pin 62 around the angle A-A' relative to the reference angular position, this information being representative of the shearing stress applied by the drilling fluid on the pin 62.

The transport means 52 includes, from upstream to downstream, a sampling head 80 for drilling fluid, a drilling fluid intake pump 82 having an inlet connected to the sampling head 80, and a drilling fluid intake pipe 84 in the measuring device 50, the intake pipe 84 being connected upstream, to an outlet of the pump 82, and downstream, to the intake opening 72.

The sampling head 80 is intended to be submerged in a circulating drilling fluid mass. Alternatively, it is bled on a drilling fluid circulation pipe.

In this example, the sampling head 80 is submerged in the receiving tub 47 to take drilling fluid emerging from the well in liquid form after filtering the solid residues in the vibrating screen 45.

Alternatively, the head 80 is mounted directly in the emptying pipe 25, upstream from the vibrating screen 45.

The head 80 is connected to an inlet of the pump 82 by an upstream pipe 86.

The pump 82 is advantageously a fluid positive displacement pump, such as a peristaltic pump, for example.

This pump 82 is capable of delivering, at its outlet in the injection pipe 84, a constant and adjustable drilling fluid flow rate sampled by the sampling head 80. This flow rate is for example between 0.1 l/min and 10 l/min.

The pump 82 is connected to the control unit 58 to be steered by said unit 58.

The intake pipe 84 comprises an upstream section 88 connected to the outlet of the pump 82, possibly an upstream three track valve 90, and a downstream section 92 emerging in the intake opening 72.

The upstream section 88 and the downstream section 92 are connected to the three track valve 90, when it is present.

The downstream section 92 extends inclined or vertical under the device 50.

It emerges at the top in the intake opening 72 while being substantially perpendicular to the axis A-A'.

The discharge means 54 comprises a discharge pipe 94, possibly a three track valve 96 and a downstream pipe 98 returning towards the retention tank 47.

The downstream pipe 94 extends substantially vertically or inclined relative to the axis A-A'. It emerges upstream in the discharge opening 74, above the measuring device 50. It emerges downstream in the three track valve 96.

In this example, the temperature and level sensors 51A, 51B are arranged in the discharge pipe 94, near and opposite the discharge opening 74.

The downstream pipe 98 connects the downstream three track valve 96 to a discharge volume of the analyzed drilling fluid, which, in this example, is formed by the retention tank 47.

The cleaning means 56 includes a cleaning fluid tank 100, an auxiliary pump 102, a sampling pipe 104 for sampling cleaning fluid in the tank 100, and an injection pipe 106 for injecting cleaning fluid in the intermediate space 64.

The cleaning means 56 also comprises an assembly 108 for purging the intermediate space 64.

The cleaning fluid contained in the tank 100 is advantageously a cleaning liquid separate from the drilling fluid. The cleaning liquid is for example water or oil used as base for the continuous oil phase mud. As will be described in more detail below, the cleaning fluid may be used to calibrate the measuring assembly 10. Therefore, the rheological properties of the cleaning fluid or a calibration fluid are well know and documented, including at various temperatures.

The sampling pipe 104 connects the tank 100 to an inlet of the auxiliary pump 102. The injection pipe 106 connects an outlet of the auxiliary pump 102 to the or each injection opening 76.

The purge assembly 108 comprises a bleed 110 connected to a source 112 of compressed gas. The bleed 110 in this example emerges in the downstream section 92 of the injection pipe 84 under the device 50. Alternatively, the bleed 110 emerges directly in the intermediate space 64 through the jacket 66.

In the example illustrated in FIG. 2, the cleaning means 56 also comprises an upstream bleed 114 connecting the upstream three track valve 90 to a discharge space formed in this example by the tank 100. The cleaning means 56 comprises a downstream bleed 116 connecting the downstream three track valve 96 to a discharge space, formed in this example by the tank 100.

The bleeds 114, 116 allow the cleaning of the downstream section 92 of the injection pipe 84 and the cleaning of the discharge pipe 94, respectively, as will be seen later.

The auxiliary pump 102 is connected to the control unit 58. It is capable of being steered to project cleaning fluid coming from the tank 100 into the intermediate space 64 through the injection pipe 106 and the injection openings 76.

The control and measuring unit 58 includes a control module 120 and a measuring module 122.

The control module 120 is connected to the pump 82, the driving mechanism 68, the three track valves 90 and 96, the auxiliary pump 102, respectively, via electrical or pneumatic control links. In this example, the control links are pneumatic.

The control module 120 is capable of steering the pump 82 to produce a plurality of successive phases of viscosity measurements, in which the pump 82 is active to pump fluid through the intermediate space 64, and a plurality of gel measurement phases, in which the pump 82 is temporarily stopped to immobilize the drilling fluid present in the intermediate space 64.

The control module 120 is also capable of steering the pump 82 to produce a cleaning phase in which the pump 82 is stopped and the cleaning means 56 is active, as will be seen later.

The measuring module 122 comprises means for recording data received from the respective sensors 51A, 51B, and 70.

As will be seen Eater, and according to the disclosure, the recording means is capable of recording, at a given frequency, all of the data coming from the sensor 70, in particular during gel measurement phases when the pump 82 is stopped.

In another exemplary embodiment, as eluded to previously, the cleaning fluid may be used to calibrate the measuring assembly 10 using the above detailed mechanism. The calibration may also be completed using non-cleaning fluid, as long its rheological properties are known. However, using a cleaning fluid, the measuring assembly 10 may be cleaned and calibrated at substantially the same or at the same time. In particular, as the measuring assembly 10 is being cleaned, which will be described in detail below, the known fluid may be measured for its rheological properties. To ensure that only the known fluid is being measured, various processes and procedure, such as purging the system for a period of time, etc., may be used to ensure that uncontaminated fluid is being measured. The measuring system 10 may then be reset or calibrated to match the results of the calibration measurements.

A measuring method according to the disclosure, implemented during drilling of a well, will now be described as an example, in reference to FIG. 1.

To perform the drilling, the drill tool 15 is driven in rotation by the surface installation 41. A drilling fluid is introduced in liquid form in the inner space 35 of the drill string 29 by the injection means 43. This fluid descends to the drill head 27, and passes into the drill pipe 13 through the drill head 27. This fluid cools and lubricates the piercing means 33. Then, the fluid collects the solid rubble resulting from the drilling and rises up through the annular space defined between the drill string 29 and the walls of the drill pipe 13, then is discharged through the emptying pipe 25 to the vibrating screen 45.

The liquid coming from the vibrating screen 45 is collected in the retention tank 47.

As illustrated by FIG. 1, part of this liquid is continuously pumped from the tank 47 towards the injection means 43 through a recycling pipe 148 to recycle the drill mud.

At the same time, the sampling head 80 is arranged in the volume of drilling fluid present in the tank 47. The measuring method according to the disclosure can then be carried out.

Figure 3:
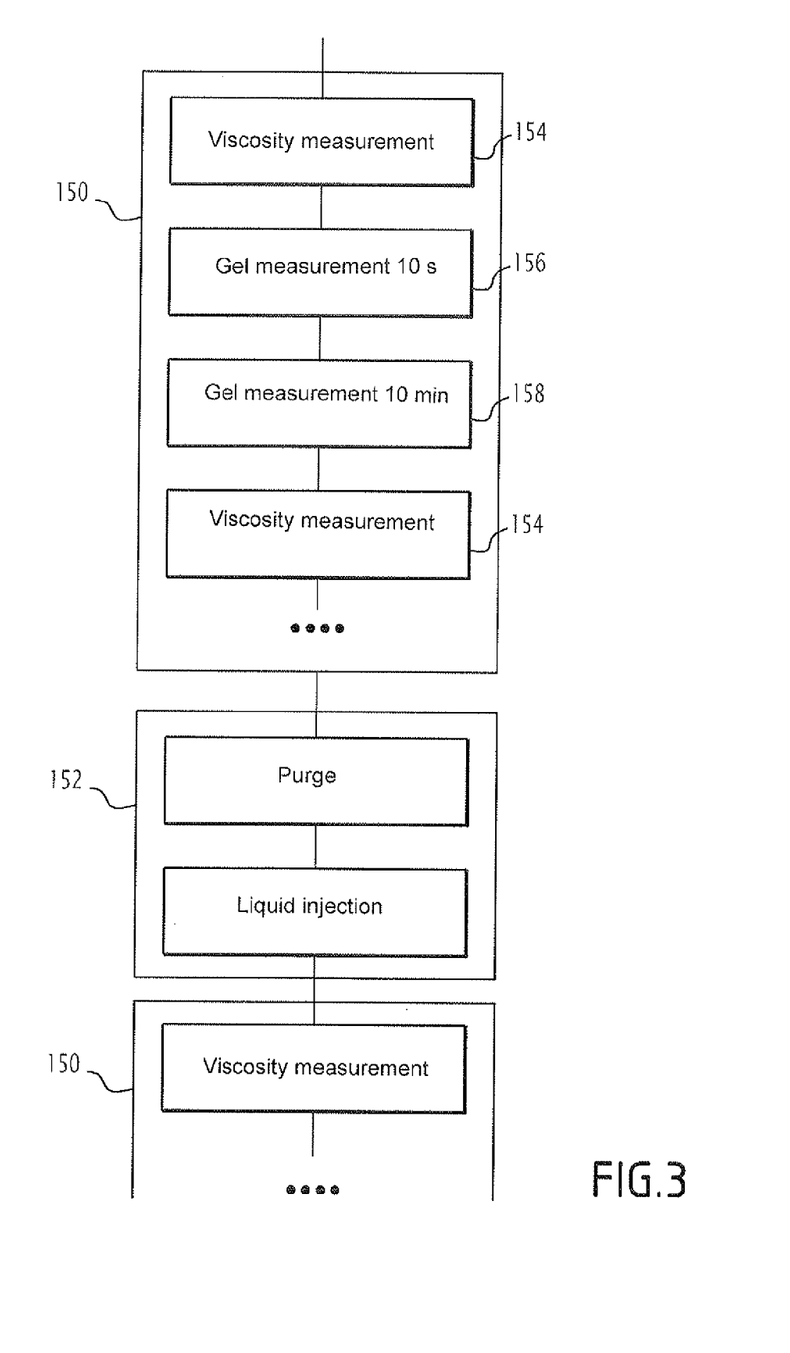
FIG. 3 is a flowchart illustrating the implementation of a first measuring method according to the disclosure.

As illustrated by FIG. 3, this method includes a plurality of measuring phases 150, and a plurality of cleaning phases 152 inserted between the measuring phases 150.

In the example shown in FIG. 3, each measuring phase 150 comprises at least a first step 154 for measuring viscosity, at least a first step 156 for measuring gel with a first chosen idle time, and at least one second step 158 for measuring gel with a second chosen idle time.

The number of viscosity measurement steps, or gel measurement steps, as well as their frequency, is programmed in the control unit 58. These steps can also be triggered manually by the user using the control unit 58.

In each step for measuring the viscosity 154, the control module 120 of the unit 58 steers the pump 82 to continuously sample drilling fluid using the sampling head 80 in the retention tank 47, for example at a flow rate greater than 0.1 l/min.

The three track valve 90 is steered to connect the upstream section 88 exclusively to the downstream section 92.

The drilling fluid passes in the upstream pipe 86, the pump 82, and rises up to the downstream section 92 of the pipe 84 through the three track valve 90.

The drilling fluid then rises up to the injection opening 72 and penetrates the intermediate space 64 between the pin 62 and the container 60.

The drilling fluid fills the intermediate space 64 and is discharged through the discharge opening 74. It then circulates through the discharge pipe 94 to the downstream valve 3 and through the downstream pipe 98.

When the level sensor 51B detects the presence of drilling fluid in the downstream pipe 94, the control module 120 steers the driving mechanism 68 to drive the rotation of the container 60 around the axis A-A' at at least a first given constant speed during a chosen measuring time.

Figure 4:
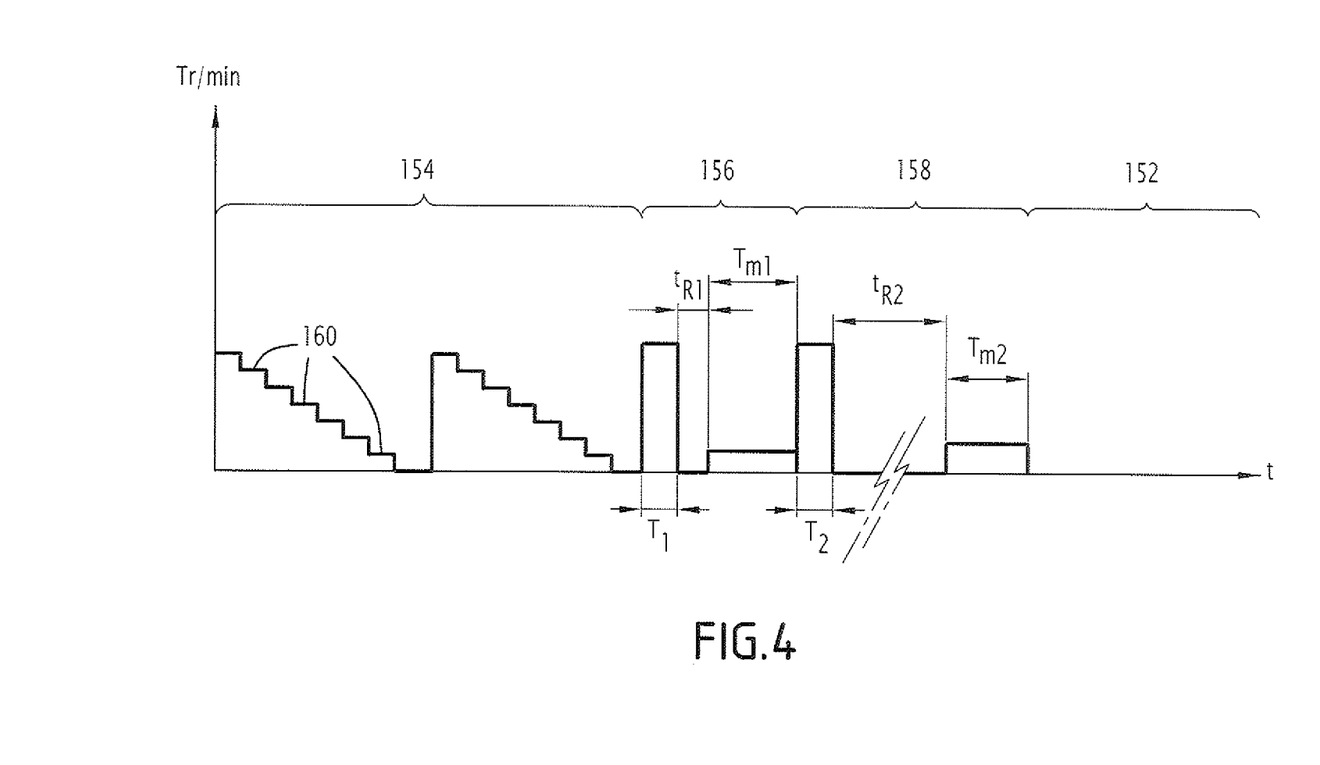
FIG. 4 is a view of a curve showing the speed of rotation of the container of the measuring assembly around its axis during different phases of the method illustrated in FIG. 3.

As shown in FIG. 4, the module 120 steers the means 68 for driving in rotation to produce a plurality of measurement levels 160 at decreasing constant speeds.

For each speed level 160 during the measuring time, the measuring module 122 collects the representative information collected by the sensor 70 connected to the pin 62.

The measuring module 122 then calculates the shearing stress for the different speeds of rotation to deduce the rheological properties of the fluid, any viscoelastic behavior thereof, based on measurements done for each level 160.

The speed at which the hollow container 60 is driven in rotation around the axis A-A' is for example greater than 400 rpm in the first level 160 and is less than 4 rpm in the last level 160.

At any moment, the measuring module 122 records the temperature of the drilling fluid measured by the sensor 51A.

When a first gel measurement step 156 must be performed, the control module 120 stops the pump 82 to immobilize the drilling fluid present in the intermediate space 64.

Then, as illustrated by FIG. 4, the control means 120 steers the mechanism 68 for driving in rotation, to drive the container 60 in rotation at a relatively high speed around the axis A-A', for example at a speed higher than 400 rpm.

Then, at the end of a first given homogenization time T1, the control module 120 stops the driving mechanism 68 to immobilize the container 60 and the fluid present in the intermediate space 64 during an idle time $T_{R1}$ for example less than 20 seconds and in particular equal to 10 seconds.

Then, the control module 120 steer the mechanism 68 for driving in rotation to drive, at a relatively low speed, advantageously less than 4 rpm, the container 60 in rotation around its axis A-A' for a given measurement time $T_{M1}$. This measurement time $T_{M1}$ is for example equal to 8 seconds.

The recording means records at a given frequency, for example greater than 1 Hertz, and in particular equal to 5 Hertz, the values measured by the sensor 70 over the entire duration of the measuring time $T_{M1}$ to determine the maximum of the measurement obtained by the sensor 70, as well as the dynamic behavior of the measurement before and after the maximum is reached.

Figure 5:
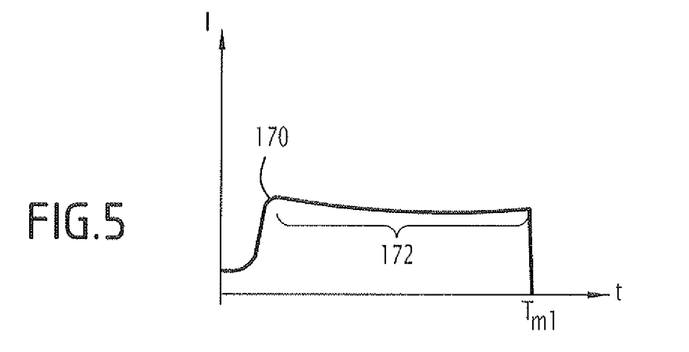
FIG. 5 is a curve showing the force applied by the drilling fluid on the pin of the measuring assembly, collected as a function of time during a first gel measurement of the drilling fluid.

This measurement is illustrated for example by FIG. 5, where the maximum is reached at point 170 and where the data obtained after the maximum in the time interval 172 is recorded at the given frequency.

Then, in step 158, a second gel measurement is done. As in step 156, the control module 120 first activates the driving mechanism 68 to drive the hollow container in rotation at a high speed around its axis A-A' during a second given homogenization time period T2.

The driving speed is greater than 400 rpm and the homogenization time is less than 20 seconds.

Then, the control module 120 stops the mechanism 68 for driving in rotation to immobilize the hollow container 60 during a second given idle time $T_{R2}$.

The duration of the second idle time $T_{R2}$ is much greater than the duration $T_{R1}$. This duration is for example longer than one minute and in particular equal to ten minutes.

Then, at the end of the second idle time, the control module 120 activates the mechanism 68 for driving in rotation to drive the hollow container 60 in rotation around its axis A-A' at a relatively low speed during a second measurement time $T_{M2}$.

This low speed is for example less than 4 rpm.

Figure 6:
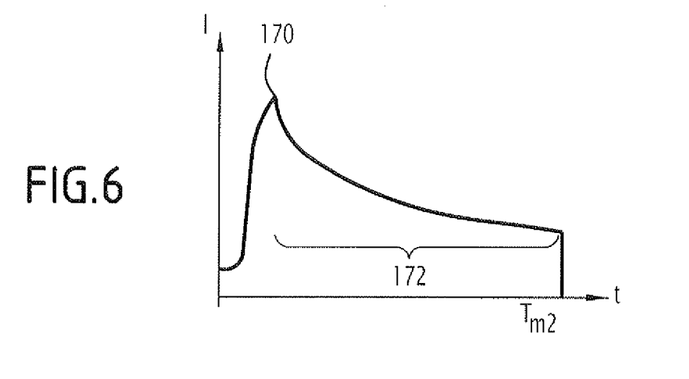
FIG. 6 is a curve similar to that of FIG. 5 during a second gel measurement of the same drilling fluid.

The measuring module 122 records at a given frequency, for example greater than 1 Hertz and in particular equal to 5 Hertz, over the entire measuring time $T_{M2}$, the data received from the sensor 70. As illustrated by FIG. 6, this makes it possible to determine the maximum 170 of the value given by the sensor 70, as well as the dynamic behavior measured after obtaining the maximum 170. In other words, in addition to only obtaining the maximum force 170, all of the force information over the interval 172 is obtained and can be provided. With this additional information, the knowledge of the maximum force 170 can be obtained and can be used as described. Furthermore, the force over time information related to the interval 172 and beyond, may also be used in extracting additional fluid parameters or information related or correlatable to fluid parameters.

As illustrated by FIG. 3, the measuring phase 150 can then comprise other steps for measuring the viscosity 154 and other gel measurement steps 156, 158.

At the end of a certain number of steps 154, 156, 158 programmed into the control means 120, or when the operator triggers it manually, a cleaning phase 152 is done.

The control module 120 then deactivates the pump 82 to stop the flow of drilling fluid through the intake pipe 84, the measuring device 50 and the discharge pump 94.

The control module 120 then activates the purge assembly to inject compressed gas coming from the source 112 through the injection bleed 110. The compressed gas penetrates the intermediate space 64 through the opening 72 and discharges the drilling fluid outside the discharge pipe 94, the three track valve 96 to the downstream pipe 98.

Once the intermediate space 64 is empty, the control module 120 steers the three track valve 190 to connect the downstream section 92 to the upstream bleed 114 and isolate the downstream section 92 from the upstream section 84.

The control module 120 then activates the auxiliary pump 102, allowing the cleaning fluid to be pumped from the tank 100, through the sampling pipe 104, the pump 102, and the cleaning fluid intake pipe 106 to each opening 76.

The intermediate space 64 having been previously purged of drilling fluid, the cleaning fluid is ejected at a high speed into the intermediate space 64. This ensures effective and rapid cleaning of the opposite surfaces of the container 60 and the pin 62.

The cleaning fluid is then discharged by gravity through the upstream section 92, the three track valve 90 to the tank 100. This ensures cleaning of the intake pipe 84.

The discharge pipe 94 can also be cleaned by steering the three track valve 96 to connect the discharge pipe 94 exclusively to the downstream bleed 116 and make the cleaning fluid circulate through the intermediate space 64, the discharge pipe 94 and the downstream bleed 116.

The cleaning fluid injection openings 76 emerge directly in the intermediate space 64 between the pin 62 and the container 60, through an opening separate from the drilling fluid injection opening 72 and separate from the drilling fluid discharge opening 74, the cleaning of the intermediate space 64 is particularly effective and requires substantially no manual intervention by the operator.

Once the cleaning phase is done, the control module 120 steers the valves 90, 96 and the pump 82 to perform a new measuring phase 150.

Figure 8:
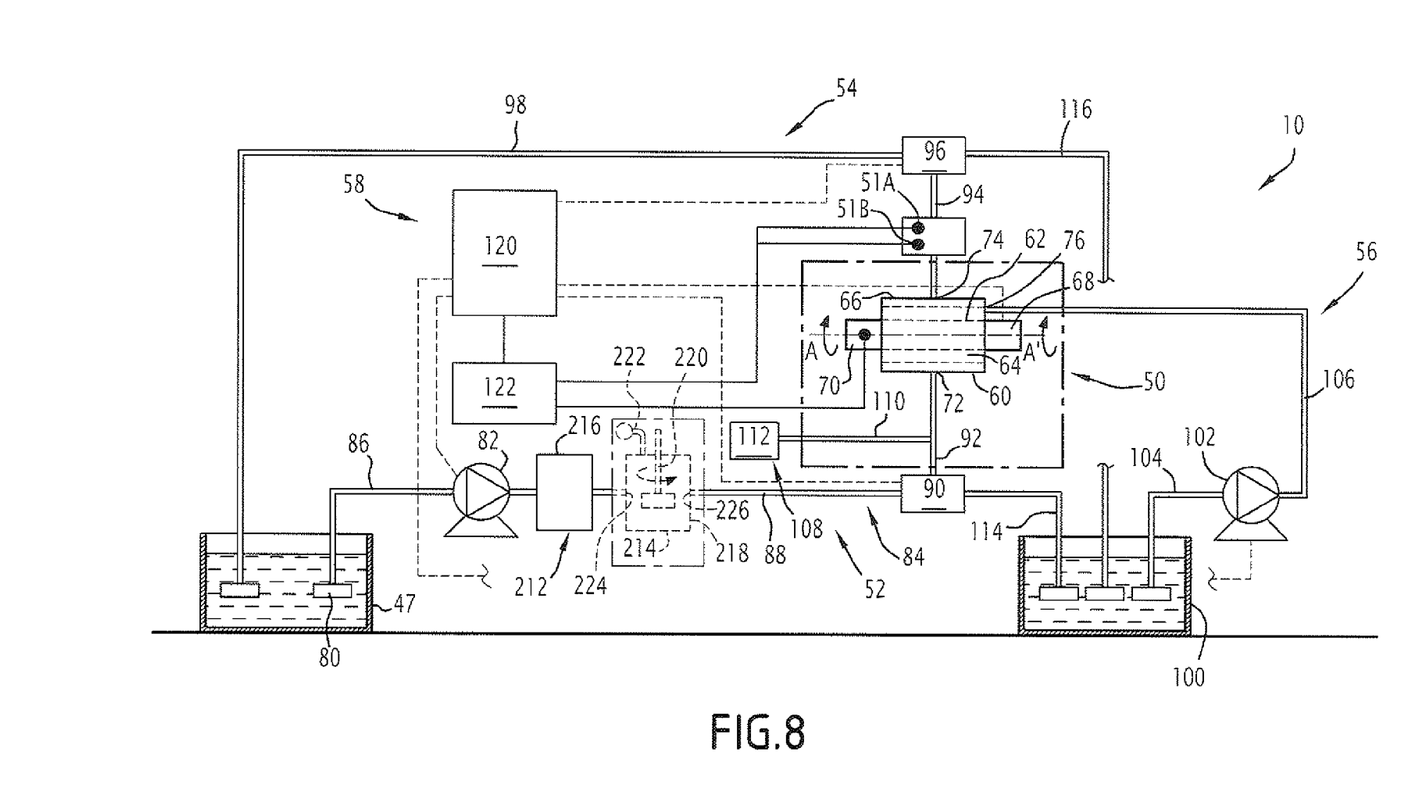
FIG. 8 is a view similar to FIG. 2 of a second measuring assembly according to the disclosure.

A second measuring assembly 210 according to the disclosure is shown in FIG. 8. Unlike the first assembly 10, the transport means 52 also comprises a module 212 for regulating the temperature of the drilling fluid and, in an alternative shown in dotted lines, a degassing module 214 for degassing the drilling fluid.

The regulating module 212 for example includes a heat exchanger capable of putting a coolant fluid in a contactless heat exchange relationship with the drilling fluid from the pump 82. The module 212 is arranged on the downstream section 88 of the intake pipe 94. It for example includes a plate exchanger.

The control module 120 is capable of making the coolant fluid circulate at a chosen temperature, to cool or heat the drilling fluid and bring it to a determined temperature.

In one alternative, the regulating module 212 comprises only heating means, such as resistances.

The degassing module 214, when it is present, is arranged on the downstream section 88 of the mud injection pipe 94, advantageously downstream from the heating module 212. It for example includes a degassing container 218, an agitator 220 arranged in the container 218, and gas discharge means 222. The container 218 delimits a drilling fluid injection inlet 224 and a degassed drilling fluid discharge outlet 226 emerging in an upper portion of the container 218.

The rotary agitator 220 is submerged in the drilling fluid circulating in the container 218. During its driving in rotation, it is capable of agitating the drilling fluid to extract the gas contained in said fluid. The extracted gas is discharged through the discharge means 222, which for example include a pipe and a pump.

Unlike the first method, when the pump 82 is activated by the control module 120, the drilling fluid from the pump 82 penetrates the module for regulating the temperature 212. The drilling fluid enters into a heat exchange relationship with the coolant or with the resistances present in this module 212. It then comes out of the module 212 at a given temperature adjusted by the control module 120.

When the degassing module 214 is present, the drilling fluid is introduced into the container 218 through the injection inlet 224. It is agitated by the agitator 220, which causes the at least partial extraction of the gas contained in the drilling fluid. The extracted gas is discharged by the discharge means 222.

The degassed drilling fluid from the module 214 is then discharged through the discharge outlet 226.

In one alternative of the measuring assemblies 10, 210, the mechanism 68 is connected to the pin 62 and the sensor 70 measures the angular displacement of the container 60 during the rotation of the pin 62.

In one alternative, the measuring method carried out using the measuring assembly 10, 210 includes a phase for calibrating the measurement as a function of the temperature and a phase for correcting the viscosity measurement obtained in each measuring step 154 as a function of the calibration done in the calibration phase.

In the calibration phase, at least two samples of drilling fluid at two given calibration temperatures, respectively, are successively introduced into the intermediate space 64, then are measured at at least one given speed of rotation of the container 60 relative to the pin 62, steered by the control module 120, as previously described for each step 154.

Figure 7:
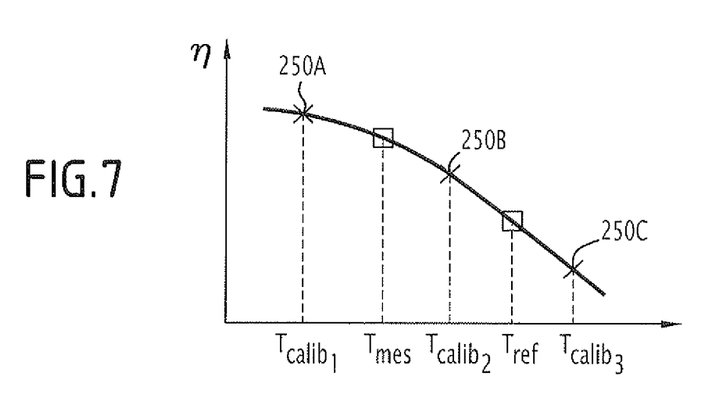
FIG. 7 is a view of a calibration curve showing the shearing stress of a drilling fluid measured at different temperatures in the assembly of FIG. 1 of a given speed of rotation of the container.

At each speed i of rotation, the shearing stress $\square_c$ measured for the different calibration temperatures $T_{calib1}$, $T_{calib2}$, $T_{calib3}$, illustrated by points 250A, 250B, 250C on the curve of FIG. 7, is then used to determine the parameters $a_i$, $b_i$, $c_i$ making up an equation connecting the value of the stress $\square(T_{ref})$ at a reference temperature $T_{ref}$, for example equal to 50° C., to the value of the stress $\square(T_{mes})$ at the effective measurement temperature.

In one application example, the equation is for example of the type:

$$\square(T_{ref}) = \square(T_{mes}) \times [a_i \times (T_{mes} - T_{ref})^2 + b_i \times (T_{mes} - T_{ref}) + c_i]$$

In one embodiment, the samples of drilling fluid at the different temperatures $T_{calib1}$, $T_{calib2}$, $T_{calib3}$ are successively manually introduced into the annular space 64 by an operator.

In one alternative, the drilling fluid at a temperature $T_{calib1}$ and pumped by the pump 82 through the injection pipe 84 to the intermediate space 64. Then the pump 82 is stopped by the control module 120.

The temperature of the fluid is measured by the probe 51A. A first measurement of the temperature $T_{calib1}$ is done for each speed of rotation to be calibrated as previously described. Then, the fluid is left idle in the intermediate space 64 to cool to a temperature $T_{calib2}$. At the temperature $T_{calib2}$, a new measurement is done. As before, the control module 120 activates the driving means 68 to drive the container 60 in rotation around the axis A-A' at the or each desired speed. This operation can then be repeated to obtain other measuring points.

In another alternative, implemented in the assembly 210 shown in FIG. 8, the drilling fluid is pumped using the pump 82, which is activated by the control module 120. Moreover, the control module 120 steers the regulating module 212 so that the temperature of the fluid coming out of the module 212 is substantially equal to the temperature $T_{calib1}$.

The measurement is then done as previously described at said first temperature $T_{calib1}$. Then, the control module 120 steers the temperature regulating module 212 so that the temperature of the fluid at the outlet of the module 212 is substantially equal to the second temperature $T_{calib2}$ distinct from the first temperature $T_{calib1}$. Another measurement in the device 50 is then done, as previously described.

Once the calibration phase is done, a phase for calculating the corrected stress value is carried out by the module 122 using the shearing stress measured at the measuring temperature as determined by the probe 51A, and calculating the shearing stress at the reference temperature $T_{ref}$ based on the equation defined above, whereof the experimental parameters $a_1$, $b_1$, $c_1$ have been determined during the calibration phase.

In another alternative, the cleaning fluid or another fluid introduced by the auxiliary pump can be introduced into the intermediate space 104 and fill it in order to calibrate the measuring device 50 in particular by determining its intrinsic drifts.

Owing to the measuring assembly 10, 210 and the measuring method according to the disclosure, as they have just been described, the rheological properties of the drilling fluid can therefore be determined reliably, simply and precisely with minimal intervention by the operator. These values can also be easily corrected based on a calibration phase that is easy to carry out in the assembly 10, 210.

The invention claimed is:

1. An online measuring assembly of rheological properties of a drilling fluid, comprising:
   a measuring device for measuring the rheological properties of the drilling fluid, including a hollow container with a central axis (A-A') and an insert arranged in the container, at least one of the container and the insert being rotatably mounted around the central axis (A-A'), the measuring device including a means for rotating one of the container and the insert around the central axis (A-A'); the container and the insert defining an intermediate measuring space between them for measuring the drilling fluid;
   a control and measurement unit for activating the means for rotating one of the container and the insert in rotation at a chosen speed to record information representative of a force applied by the drilling fluid on the other of the container and the insert during the rotation of one of the container and the insert;
   wherein the assembly includes:
   an intake pipe for taking the drilling fluid to be measured in the intermediate measuring space and a discharge pipe distinct from the intake pipe for discharging the drilling fluid outside the intermediate measuring space;
   a pump having an inlet connected to a drilling fluid sampling head in a drilling fluid volume and an outlet connected to the intake pipe to pump the drilling fluid outside the sampling head towards the intermediate measuring space,
   wherein the control and measuring unit includes a means for steering the pump for activating the pump in a first measuring phase of the measuring device to continuously inject the drilling fluid at a given flow rate into the intermediate measuring space, and wherein the assembly is configured to immobilize the drilling fluid in the intermediate measuring space during a predetermined time, then trigger a second measuring phase similar to the first measuring phase.

2. The assembly according to claim 1, further including an injection pipe for injecting a cleaning fluid, separate from the intake pipe and the discharge pipe, the injection pipe emerging in the intermediate measuring space, the assembly advantageously having an auxiliary pump for injecting the cleaning fluid having an outlet connected to the injection pipe.

3. The assembly according to claim 2, further including a means for injecting a pressurized purge gas into the intermediate measuring space, for ejecting the drilling fluid present in the intermediate measuring space before said injecting the cleaning fluid through the injection pipe.

4. The assembly according to claim 1, further including a module for regulating a temperature of the drilling fluid brought into the intermediate measuring space, the temperature regulating module advantageously being inserted between the sampling head and the container.

5. The assembly according to claim 1, further including a degassing module, for extracting a gas present in the drilling fluid to evacuate it outside the drilling fluid, the degassing module being inserted between the sampling head and the container.

6. The assembly according to claim 1, wherein the control and measuring unit further includes means for recording a temporal variation of the information representative of the force applied by the drilling fluid on the other of insert and the container, for continuously said recording the temporal variation of the representative information during the immobilization of the drilling fluid.

7. A method for online measurement of rheological properties of a drilling fluid, of a type comprising a plurality of following steps:
providing an assembly comprising:
a measuring device for measuring the rheological properties of the drilling fluid including a hollow container with a central axis (A-A') and an insert arranged in the container, at least one of the container and the insert being rotatably mounted around the central axis (A-A'), the measuring device including a means for rotating of one of the container and the insert around the central axis (A-A'); the container and the insert defining an intermediate measuring space between them for measuring the drilling fluid;
a control and measurement unit for activating the means for rotating one of the container and the insert in rotation at a chosen speed and recording information representative of a force applied by the drilling fluid on the other of the container and the insert during rotation of one of the container and the insert;
a fluid intake pipe for taking the drilling fluid to be measured in the intermediate measuring space and a discharge pipe distinct from the fluid intake pipe for discharging the drilling fluid outside the intermediate measuring space;
a pump having an inlet connected to a drilling fluid sampling head in a drilling fluid volume and an outlet connected to the fluid intake pipe to pump the drilling fluid outside the sampling head towards the intermediate measuring space;
during a first measuring phase, activating the pump to continuously pump the drilling fluid from the sampling head, through the fluid intake pipe in the intermediate measuring space, the drilling fluid being evacuated outside the intermediate measuring space through the discharge pipe,
immobilizing the drilling fluid in the intermediate measuring space;
driving in the rotation around the central axis (A-A'), at at least one given speed, one of the container and the insert using the means for rotating, while the fluid is immobilized;
measuring the information representative of the force applied by the drilling fluid on the container and the insert when one of the container and the insert is driven in the rotation around the central axis (A-A');
performing a second measuring phase similar to the first measuring phase.

8. The method according to claim 7, further including, after said measuring the information representative of the force applied by the drilling fluid, an injection of a cleaning fluid in the intermediate measuring space through an injection pipe separate from the fluid intake pipe and the discharge pipe, the injection pipe emerging in the intermediate measuring space.

9. The method according to claim 8, further including, before said injecting the cleaning fluid, a step for purging the intermediate measuring space using a pressurized gas to empty the drilling fluid present in the intermediate measuring space before said injecting the cleaning fluid.

10. The method according to claim 7, further including a step for regulating a temperature of the drilling fluid at a temperature chosen in a module for regulating the temperature arranged between the sampling head and the container.

11. The method according to claim 7, further including a degassing step of a gas present in the drilling fluid to evacuate said gas outside the drilling fluid, the degassing step being performed in a degassing module positioned between the sampling head and the container.

12. The method according to claim 7, further including a calibration phase for the measurement of the rheological properties of the drilling fluid, at said at least one given speed of the rotation of one of the container and the insert, wherein the measurement of the rheological properties depends on a temperature, the calibration phase including:
providing successively in the intermediate measuring space the drilling fluid at least two distinct calibration temperatures, and
for each calibration temperature of the distinct calibration temperatures, measuring the the representative information of the force at the at least one given speed,
determining at least one calibration parameter of an equation connecting the representative information of the force determined at one measurement temperature to the representative information of the force calculated at a reference temperature different from the one measurement temperature, the or each calibration parameter being obtained based on the representative information of the force measured at said each calibration temperature,
each measuring phase fluid comprising measuring the representative information of the force applied by the drilling fluid brought into the intermediate measuring space, and measuring the one measurement temperature of the drilling fluid, the method further comprising a phase for calculating the representative information at the reference temperature, based on the representative information measured at the one measurement temperature and an equation determined in the calibration phase.

13. The method according to claim 12, wherein the calibration phase further includes:
immobilizing the fluid in the intermediate measuring space,
measuring the information representative of the force applied by the drilling fluid present at a first calibration temperature on the other of the container and the insert when one of the container and the insert is driven in the rotation around the central axis (A-A'),
cooling the drilling fluid present in the intermediate measuring space, then
measuring the information representative of the force applied by the drilling fluid present in the intermediate measuring space at at least one second calibration temperature lower than the first calibration temperature on the other of the container and the insert when one of the container and the insert is driven in the rotation around the central axis (A-A').

14. The method according to claim 12, further including at least one phase for measuring a gel, including the following steps:
stopping the pump, driving the drilling fluid present in the intermediate measuring space in rotation at a first speed for a given homogenization time, while the pump is stopped immobilizing one of the container and the insert for a given idle time, driving one of the container and the insert in rotation at a second speed lower than the first speed for a given measurement time, while the pump is stopped measuring the information representative of the force applied by the drilling fluid on the other of the container and the insert for the given measuring time to determine the maximum value of the representative information as a function of the time during the given measuring time, recording, at a given frequency, representative information measured during the entire given measuring time to obtain the temporal variation of the representative information before and after the maximum value.

* * * * *